United States Patent
Lee et al.

(10) Patent No.: US 11,957,570 B2
(45) Date of Patent: *Apr. 16, 2024

(54) INTRAOCULAR LENS HAVING CLOSED-LOOP HAPTIC STRUCTURES

(71) Applicant: ALCON INC., Fribourg (CH)

(72) Inventors: Sung Kyu Lee, Euless, TX (US); Stephen John Collins, Fort Worth, TX (US); Ian Michael Marks, Dallas, TX (US); Jonathan David Mccann, Van Alstyne, TX (US); Jian Liu, Keller, TX (US); Douglas Brent Wensrich, Bedford, TX (US); Stephen J. Van Noy, Southlake, TX (US)

(73) Assignee: Alcon Inc., Fribourg (CH)

(*) Notice: Subject to any disclaimer, the term of this patent is extended or adjusted under 35 U.S.C. 154(b) by 0 days.

This patent is subject to a terminal disclaimer.

(21) Appl. No.: 17/351,433

(22) Filed: Jun. 18, 2021

(65) Prior Publication Data

US 2021/0307896 A1 Oct. 7, 2021

Related U.S. Application Data

(63) Continuation of application No. 16/174,476, filed on Oct. 30, 2018, now Pat. No. 11,065,108.

(Continued)

(51) Int. Cl.
*A61F 2/16* (2006.01)

(52) U.S. Cl.
CPC ........ *A61F 2/16* (2013.01); *A61F 2002/1681* (2013.01); *A61F 2002/1683* (2013.01);

(Continued)

(58) Field of Classification Search
CPC ............ A61F 2/1694; A61F 2002/1681; A61F 2002/1683; A61F 2002/1686;

(Continued)

(56) References Cited

U.S. PATENT DOCUMENTS

| 4,249,271 A | * | 2/1981 | Poler .................... A61F 2/16 623/6.41 |
| 4,990,159 A | | 2/1991 | Kraff |

(Continued)

FOREIGN PATENT DOCUMENTS

| EP | 0592813 A1 | 4/1994 |
| EP | 2042124 A1 | 4/2009 |

(Continued)

*Primary Examiner* — Javier G Blanco

(57) ABSTRACT

An ophthalmic device includes an optic including an optic axis and a closed-loop haptic structure coupled to the optic via a frame surrounding the optic, the closed-loop haptic structure including a closed loop extending from first and second attachment points to the frame. The closed loop includes a first hinge and a second hinge. The first hinge has a first section having a first component extending in a first angular direction, a second section having a second component extending in a second angular direction opposite to the first angular direction, and a first connecting section between the first section and the second section. The second hinge has a third section having a third component extending in the second angular direction, a fourth section having a fourth component extending in the first angular direction, the fourth section being connected to the second section to form the closed loop.

15 Claims, 5 Drawing Sheets

Related U.S. Application Data

(60) Provisional application No. 62/579,969, filed on Nov. 1, 2017.

(52) U.S. Cl.
CPC ............... *A61F 2002/1686* (2013.01); *A61F 2002/16901* (2015.04); *A61F 2002/16905* (2015.04); *A61F 2/1694* (2013.01); *A61F 2220/0091* (2013.01)

(58) Field of Classification Search
CPC .......... A61F 2002/16901; A61F 2002/169053; A61F 2/1648
See application file for complete search history.

(56) References Cited

U.S. PATENT DOCUMENTS

| | | | |
|---|---|---|---|
| 6,409,762 B1 * | 6/2002 | Pynson | A61F 2/1613 623/6.47 |
| 7,150,760 B2 | 12/2006 | Zhang | |
| 2006/0161252 A1 * | 7/2006 | Brady | A61F 2/1629 623/6.37 |
| 2008/0109077 A1 | 5/2008 | Bos | |
| 2010/0286772 A1 | 11/2010 | Privat | |
| 2015/0272725 A1 | 10/2015 | Camargos | |

FOREIGN PATENT DOCUMENTS

| | | | |
|---|---|---|---|
| FR | 2944428 A1 * | 10/2010 | ........... A61F 2/1602 |
| WO | WO-2015148673 A1 * | 10/2015 | ........... A61F 2/1613 |
| WO | 2017116357 A1 | 7/2017 | |

\* cited by examiner

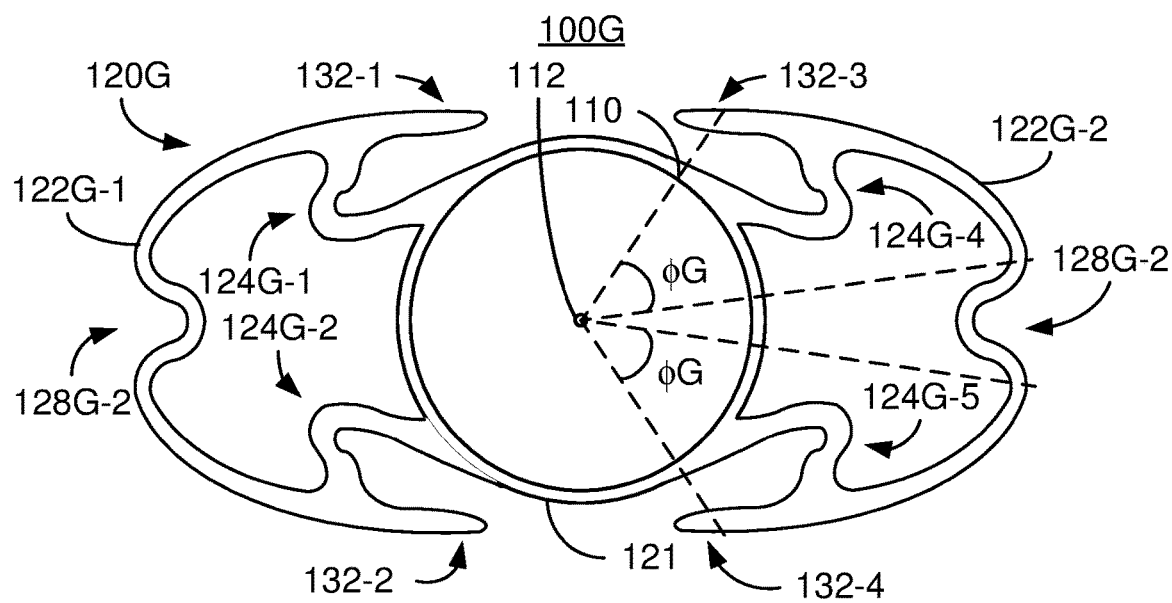
FIG. 7
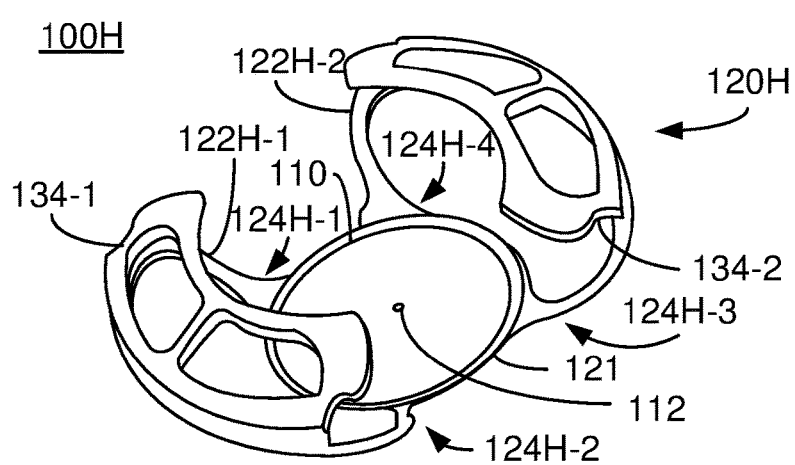
FIG. 8A
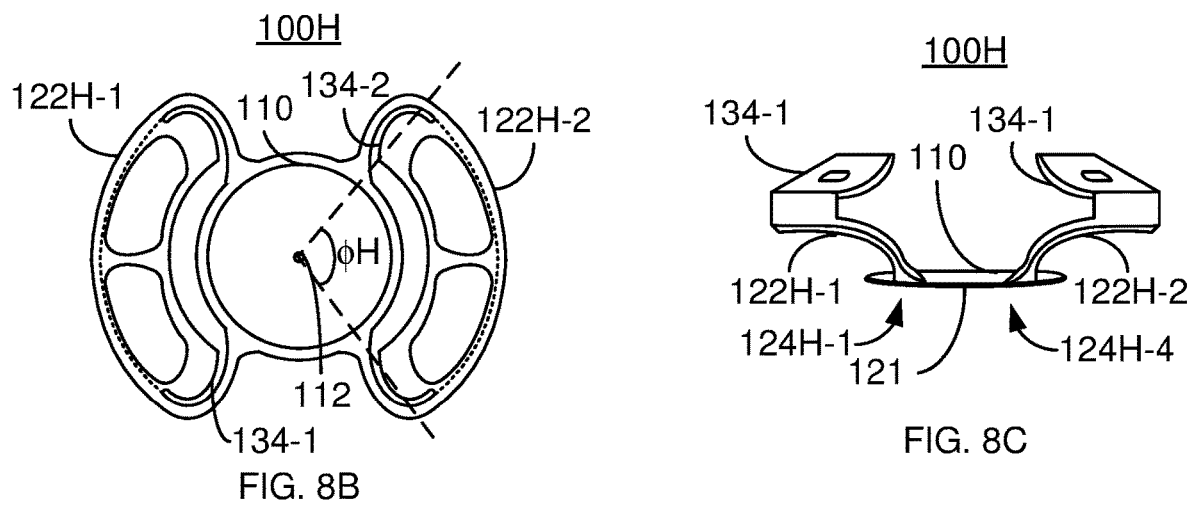
FIG. 8B
FIG. 8C

INTRAOCULAR LENS HAVING CLOSED-LOOP HAPTIC STRUCTURES

PRIORITY CLAIM

This application is a continuation of U.S. Non-Provisional patent application Ser. No. 16/174,476, filed on Oct. 30, 2018 and claims the benefit of priority of U.S. Provisional Patent Application Ser. No. 62/579,969 titled "INTRAOCULAR LENS HAVING CLOSED-LOOP HAPTIC STRUCTURES," filed on Nov. 1, 2017, whose inventors are Sung Kyu Lee, Stephen John Collins, Ian Michael Marks, Johnathan David McCann, Jian Liu, Douglas Brent Wensrich and Stephen J. Van Noy, which is hereby incorporated by reference in its entirety as though fully and completely set forth herein.

FIELD

The present disclosure relates generally ophthalmic lenses and, more particularly, to intraocular lenses having closed-loop haptic structures.

BACKGROUND

Intraocular lenses (IOLs) may be implanted in patients' eyes to replace a patient's natural lens. An IOL typically includes (1) an optic that corrects the patient's vision (e.g., typically via refraction or diffraction), and (2) haptics that constitute support structures that hold the optic in place within the patient's eye (e.g., within capsular bag). In general, a physician selects an IOL for which the optic has the appropriate corrective characteristics for the patient. During ophthalmic surgery, often performed for conditions such as cataracts, the surgeon implants selected IOL by making an incision in the capsular bag of the patient's eye (a capsulorhexis) and inserting the IOL through the incision. Typically, the IOL is folded for insertion into the capsular bag via a corneal incision and unfolded once in place within the capsular bag. During unfolding, the haptics may expand such that a small section of each bears on the capsular bag, retaining the IOL in place.

Although existing IOLs may function acceptably well in many patients, they also have certain shortcomings. For example, existing IOL design may include haptics that cause striae, or folds, in the posterior capsular bag. Such striae may result from the haptics having a relatively small angle of contact with the capsular bag. Because striae may negatively impact patient outcomes (e.g., by resulting in increased posterior capsular opacification (PCO) by providing a mechanism for the growth and/or migration of cells), haptic designs that reduce striae are desirable. Moreover, such designs should also have a volume and foldability conducive to maintaining acceptably small incision sizes (e.g., 3 mm or less) as larger incision may adversely affect the patient's recovery.

Accordingly, what is needed is an improved IOL that may address PCO (e.g., by reducing striae) without significantly complicating implantation.

SUMMARY

An ophthalmic device includes an optic including an optic axis and a closed-loop haptic structure coupled to the optic via a frame surrounding the optic, the closed-loop haptic structure including a closed loop extending from first and second attachment points to the frame. The closed loop includes a first hinge and a second hinge. The first hinge has a first section having a first component extending in a first angular direction, a second section having a second component extending in a second angular direction opposite to the first angular direction, and a first connecting section between the first section and the second section. The second hinge has a third section having a third component extending in the second angular direction, a fourth section having a fourth component extending in the first angular direction, the fourth section being connected to the second section to form the closed loop.

In certain embodiments, the closed-loop haptic structure described herein may provide one or more technical advantages. For example, the closed-loop haptic structure described herein may result in fewer striae and reduced PCO, yet may be relatively easily implanted. Consequently, performance of the ophthalmic device may be improved. As another example, the closed-loop haptics described herein, when compressed in capsular bag, may deform such that the space between adjacent haptics id filled, thereby allowing the haptics to deform radially. As a result, the closed-loop haptic structure described herein may exhibit mechanical stability across a range of capsular bag sizes.

BRIEF DESCRIPTION THE DRAWINGS

For a more complete understanding of the present disclosure and the advantages thereof, reference is now made to the following description taken in conjunction with the accompanying drawings in which like reference numerals indicate like features and wherein:

FIG. 7 depicts another exemplary embodiment of an ophthalmic device having a closed-loop haptic structure; and FIGS. 8A-8C depict various views of another exemplary embodiment of an ophthalmic device having a closed-loop haptic structure.

The skilled person in the art will understand that the drawings, described below, are for illustration purposes only. The drawings are not intended to limit the scope of the applicant's disclosure in any way.

DETAILED DESCRIPTION

The exemplary embodiments relate to ophthalmic devices such as intraocular lenses (IOLs). The following description is presented to enable one of ordinary skill in the art to make and use the invention and is provided in the context of a patent application and its requirements. Various modifications to the exemplary embodiments and the generic principles and features described herein will be readily apparent. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. Thus, the present invention is not intended to be limited to the embodiments shown, but is to be accorded the widest scope consistent with the principles and features described herein.

In general, the present disclosure relates to an ophthalmic device including an optic and a closed-loop haptic structure coupled to the optic via a frame surrounding the optic, the closed-loop haptic structure including a closed loop extending from first and second attachment points to the frame. The closed loop includes a first hinge and a second hinge. The first hinge has a first section having a first component extending in a first angular direction, a second section having a second component extending in a second angular direction opposite to the first angular direction, and a first connecting section between the first section and the second section. The second hinge has a third section having a third component extending in the second angular direction, a fourth section having a fourth component extending in the first angular direction, the fourth section being connected to the second section to form the closed loop.

Figure 1A:
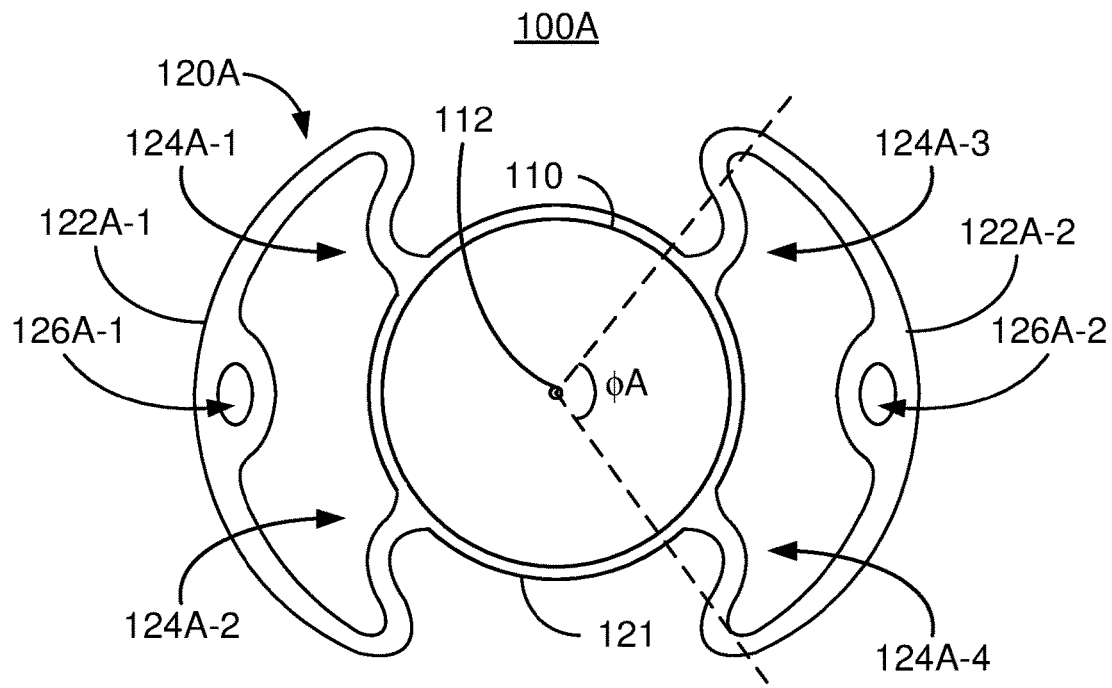
FIGS. 1A-1D depict various views of an exemplary embodiment of an ophthalmic device having a closed-loop haptic structure.
Figure 1B:
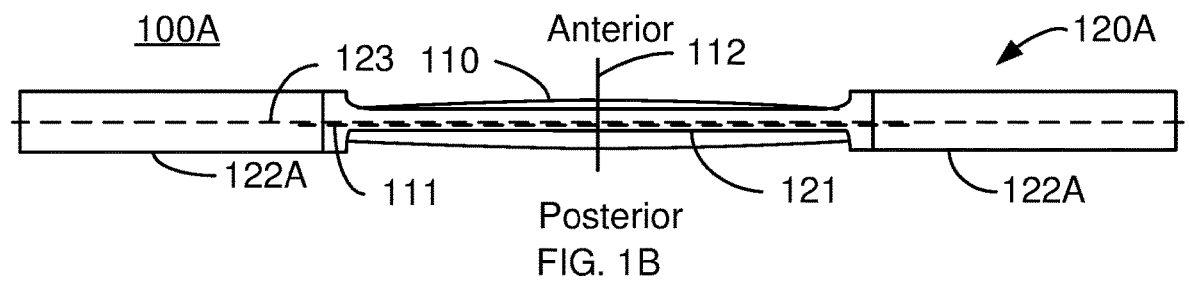
Figure 1C:
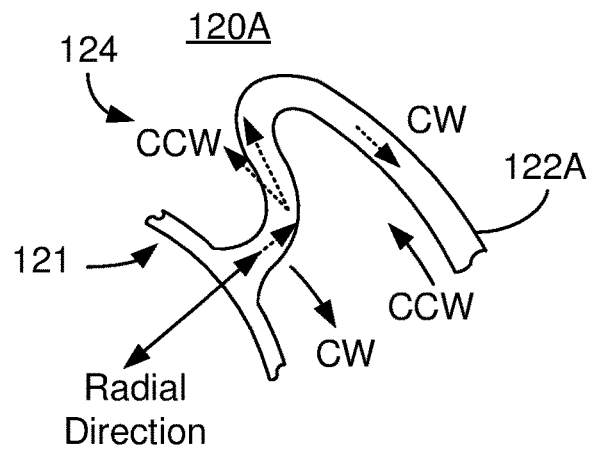
Figure 1D:
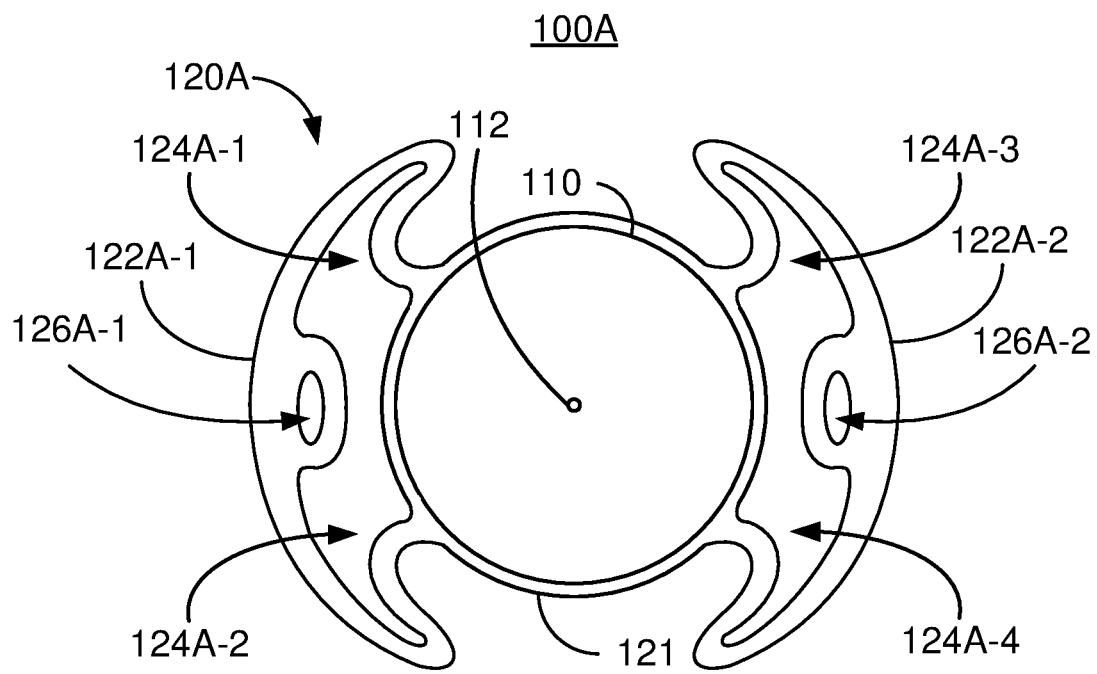

FIGS. 1A-1D depict various views of an exemplary embodiment of an ophthalmic device 100A having an optic 110 and a closed-loop haptic structure 120A. For simplicity, the ophthalmic device 100A is also referred to as an IOL 100A. FIG. 1A depicts a plan view of the IOL 100A, while FIG. 1B depicts a side view of the IOL 100A. FIG. 1C depicts a portion of the IOL 100A. FIG. 1D depicts a plan view of the IOL 100A under the influence of a compressive force. For clarity, FIGS. 1A-1D are not to scale and not all components may be shown.

The optic 110 is an ophthalmic lens 110 that may be used to correct a patient's vision. For example, the optic may be a refractive and/or diffractive lens. The optic 110 may be a monofocal lens, multifocal lens and/or a toric lens. The anterior and/or posterior surface of the optic 110 may thus have features including but not limited to a base curvature and diffraction grating(s). The optic 110 may refract and/or diffract light to correct the patient's vision. The optic 110 has an optic axis 112 that is out of the plane of the page in FIG. 1A and a centerline 111 shown in FIG. 1B that is between the anterior and posterior surfaces. The optic 110 is depicted as having a circular footprint in the plan view of FIG. 1A. In other embodiments, the optic 110 may have a differently shaped footprint. In some embodiments, the optic 110 may also include other features that are not shown. The optic 110 may be formed of one or more of a variety of flexible optical materials. For example, the optic 110 may include but is not limited to one or more of silicone, a hydrogel and an acrylic such as AcrySof®.

The closed-loop haptic structure 120A is a support structure used to hold the ophthalmic device 100A in place in the capsular bag of a patient's eye (not explicitly shown). The closed-loop haptic structure 120A includes a frame 121 (or ring), closed loops 122A-1 and 122A-2, hinges 124A-1, 124A-2, 124A-3 and 124A-4 and manipulation structures 126A-1 and 126A-2. The closed-loop haptic structure 120A also has a centerline 123 between the anterior and posterior edges.

The frame 121 couples the closed-loop haptic structure haptic 120A with the optic 110. The inner portion of the frame 121 may be desired to match the shape of the optic 110. Thus, the inner edge of the frame 121, shown as circular in FIG. 1A, may have a different shape in embodiments in which the optic is not circular. The outer edge of the frame 121 can but need not match the inner edge (i.e., the frame 121 may have a non-uniform width). In some embodiments, the closed-loop haptic structure 120A and the optic 110 may be molded together. Thus, the optic 120A and haptic may form a single monolithic structure. In other embodiments, the frame 121 may be otherwise attached to the optic 110. For example, the frame 121 may be bonded to or molded around a preexisting optic 110.

The closed loops 122A-1 and 122A-2 (collectively or generically termed closed loops 122A) contact the capsular bag when implanted in a patients eye and serve to retain the IOL 100A in a desired position in the patient's eye. Each of the loops 122A spans an angle, $\phi$A. As used herein, the angle spanned by a haptic loop represents the angular span over which the loop is intended to contact the capsular bag when implanted in a patient's eye. In certain embodiment, the angle $\phi$A is greater than ninety degrees. For example, the angle $\phi$A may be at least one hundred and twenty degrees in some cases. Consequently, the loops 122A may contact the capsular bag over a large angle. The capsular bag may thus be extended over a larger volume. The loops 122A-1 and 122A-2 may thus stretch the capsular bag over a significantly larger region than for haptics having open arms. This may reduce striae and, therefore, PCO.

Each of the closed loops 122A includes one or more hinges 124A-1, 124A-2, 124A-3 and 124A-4 (collectively or generically labeled 124). Although four hinges 124 (two for each loop 122A) are shown, alternative embodiments may include any suitable number of hinges (e.g., each loop 122A-1 and 122A-2 may include one hinge and one connection to the frame 121).

The hinges 124 are configured such that a portion of the closed loop 122A extends past the attachment point to the frame 121. In the embodiment shown in FIG. 1, the closed loops 122A extend past the attachment point. Thus, a hinge 124 may have a first section having a component that extends in one direction (e.g., the counter clockwise (CCW) direction), a second section having a component that extends in the opposite direction (e.g., the clockwise (CW) direction), and a connecting section between the first and second sections. In certain embodiments, the connecting section has a bend that may be close to one hundred and eighty degrees. Additionally, the bend may include the portion of the loop 122A that extends furthest past the attachment point (as depicted in FIG. 1C). The hinge 124 is connected to the frame 121 at or near the radial direction.

As one example, the hinge 124 may include a first section that has a component extending in the CCW direction. In FIG. 1C, the direction of the first section and the CCW direction are each shown by dotted arrows. For example, the component extending in the CCW direction may span less than forty-five degrees. As another example, the component extending in the CCW direction may span less than twenty degrees. The hinge 124 may additionally include a second section that has a component extending in the CW direction. In FIG. 1C, the direction of the second section is the same as the CW direction and both are shown by a single dotted arrow. In alternative embodiments, the second section of the hinge 124 may be oriented within twenty degrees of the CW direction. The hinge 124 may additionally include a connecting section extending between the above-discussed first and second sections. In certain embodiments, the connecting section may include a bend near one hundred and eighty degrees.

In certain embodiments, the hinge 124 may be connected to the frame 121 (at the attachment point) by a component extending substantially in the radial direction (e.g., extending between the attachment point and the above-described first section of the hinge 124). In other embodiments, such component may deviate from the radial direction in either the CW direction or the CCW direction. For example, the connection between the first component of the hinge 124 and the attachment point may be within sixty degrees of the radial direction. As another example, the connection between the first component of the hinge 124 and the attachment point may be within forty-five degrees of the radial direction. As another example, the connection between the first component of the hinge 124 and the attachment point may be within twenty degrees of the radial direction.

The hinges 124A-1 through 124A-4 may be configured such that the closed-loop haptic structure 120A may be compressed without significant motion in the anterior or posterior direction. As used herein, the anterior direction may refer to a direction extending away from the retina when implanted in the eye and the posterior direction may be a direction extending toward the retina when implanted in the eye. FIG. 1D depicts the closed-loop haptic structure 120A under a compressive force. Because of the hinges 124A-1, 124A-2, 124A-3 and 124A-4, the compression has caused the connecting section of each hinge 124 to compress, which brings the first and second sections of the hinges 124 closer together. As a result, a portion of the loops 122A-1 and 122A-2 extend further past the connection to the frame 121 than in the uncompressed state shown in FIG. 1A. The outer edges of the loops 122A also move closer to the optic axis 112. Although it is possible for the optic 110 to move in the anterior or posterior direction due to the compressive force, this tendency may be mitigated by the presence of the hinges 124.

To further address motion of the optic 110 along the optic axis 112 in response to a compression, the optic 110 may have a particular location with respect to the closed-loop haptic 120. FIG. 1B depicts the center line 111 of the optic and the centerline 123 of the closed-loop haptic structure 120A. Although termed centerlines, one of ordinary skill in the art will recognize that lines 111 and 123 generally correspond to planes. As shown in FIG. 1B, the centerline 111 of the optic 110 is closer to the posterior side than is the centerline 123 of the close-loop haptic structure 120A. For example, if the entire thickness of the IOL 100A in the direction parallel to the optic axis 112 is 0.5 mm, then the centerline 111 may be offset from the centerline 123 by 0.05-0.1 mm. The bottom/posterior edge of the optic 110 may be close to the bottom edge of the closed-loop haptic structure 120A. However, the bottom of the optic 110 may not extend lower/in a more posterior direction than the bottom of the closed-loop haptic structure 120A. Because its centerline is lower, if the optic 110 does move with respect to the haptic 120 due to a compressive force, the optic 110 moves in the posterior direction. As a result, a patient's eye is less likely to be damaged by motion of the optic 110.

In certain embodiments, the closed loops 122A-1 and 122A-2 each additionally include a manipulation structure 126A-1 and 126A-2 (collectively manipulation structures 126A). In the depicted embodiment, the manipulation structures 126A are apertures, which may allow a surgeon to insert a tool (e.g., forceps, not shown) in order to maneuver the IOL 100. In certain embodiments, the manipulation structures 126A may be located on the inner portion of the loops 122A-1 and 122A-2 (the edge located toward the optic 110) rather than the outer edge (the edge located away from the optic 110).

In certain embodiments, the closed loop haptic structure 120A may include sharp corners (as depicted in FIG. 1B). For example, both the loops 122A and the frame 121 may have sharp edges. As a result, the optic 110 may be surrounded on all sides by sharp edges. These sharp edges may also reduce the probability of cells migrating to the optic 110 from any side, which may further reduce the incidence of PCO.

Use of the IOL 100A may improve patient outcomes. The above-described closed loop haptic structures 120A may have a large angle (I)A, allowing haptic structures 120 to contact a larger portion of and better extend the capsular bag. This may not only improve the axial and rotational stability of the IOL 100A, but also may reduce the formation of striae in the capsular bag. Striae reduction, as discussed above, may reduce the incidence of PCO and therefore may improve patient outcomes. Additionally, sharp edges for the closed-loop haptic structure 120A may further reduce the incidence of PCO. Furthermore, hinges 124A-1, 124A-2, 124A-3 and 124A-4 allow the closed-loop haptic structure 120A to respond predictably to compression, which may allow the optic 110 to remain in a substantially constant plane in response to a compression (allowing for better refractive outcomes).

Figure 2:
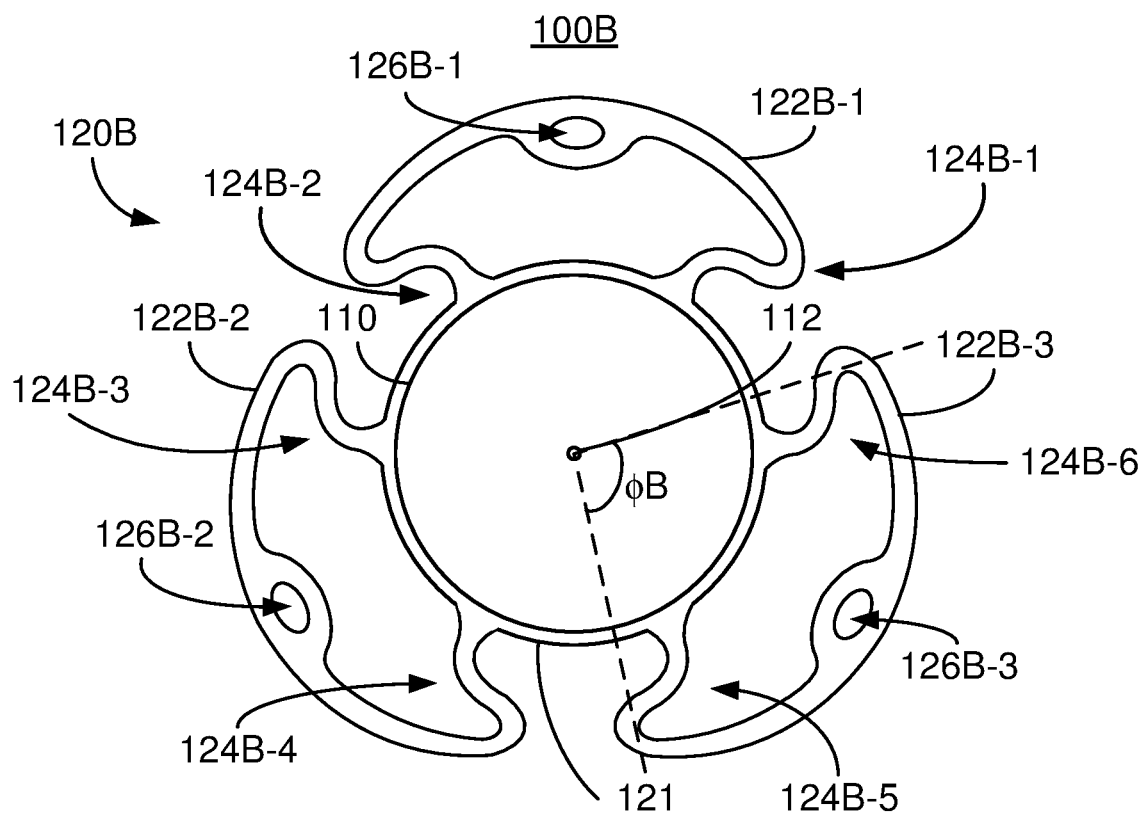
FIG. 2 depicts another exemplary embodiment of an ophthalmic device having a closed-loop haptic structure.

FIG. 2 depicts another exemplary embodiment of an ophthalmic device 100B having an optic 110 and a closed-loop haptic structure 120B. For simplicity, the ophthalmic device 100B is also referred to as an IOL 100B. The IOL 100B is similar to the IOL 100A and analogous components have similar labels. IOL 100B includes an optic 110 and closed-loop haptic structure 120B that are analogous to the optic 110 and closed-loop haptic structure 120A of FIGS. 1A-1D. Because optic 110 of IOL 100B is substantially the same as the optic 110 of IOL 100A, the optic 110 of IOL 100B will not be separately described with regard to FIG. 2. For clarity, FIG. 2 is not to scale and not all components may be shown.

Like the closed loop haptic structure 120A of IOL 100A, the closed-loop haptic structure 120B of IOL 100B may include a frame 121; closed loops 122B-1, 122B-2 and 122B-3 (collectively or generically 122B); hinges 124B-1, 124B-2, 124B-3, 124B-4, 124B-5 and 124B-6 (collectively or generically hinges 124B); centerline (not shown) and manipulation structures 126B-1, 126B-2, and 126B-3 (each of which are analogous to corresponding structures of IOL 100A). With regard to the hinges 124B, they may be configured and function in an analogous manner to the hinges 124A of IOL 100A. Similarly, manipulation structures 126B-1, 126B-2 and 126B-3 may be configured and function in an analogous manner to the manipulation structures 126A-1 and 126A-2 of IOL 100A.

The primary difference between IOL 100B and IOL 100A is that, because IOL 100B includes a haptic structure 120B having three closed loops 122B-1, 122B-2 and 122B-3 as opposed to two, each of the loops 122B may span an angle φB that is smaller than the angle φA described above with regard to IOL 100A. However, in certain embodiment, the angle φB may still be at least ninety degrees. The combination of the loops 122B may span a total angle of substantially the same as or greater than that of the angled spanned collectively by loops 122A. In other embodiments, the IOL 100B may have a larger number of loops 122B.

Although IOL 100B is depicted and described as having three loops 122B, the present disclosure contemplated IOL 100B having any suitable number of loops (e.g., four, five, six or more loops). Moreover, the span of the angle φB for each loop may correspond with the number of loops (with the angle ϕB decreasing as the number of loops increases).

For substantially the same reasons as discussed above with regard to IOL 100A, IOL 100B may improve patient outcomes by reducing incidence of PCO and improving refractive outcomes.

Figure 3:
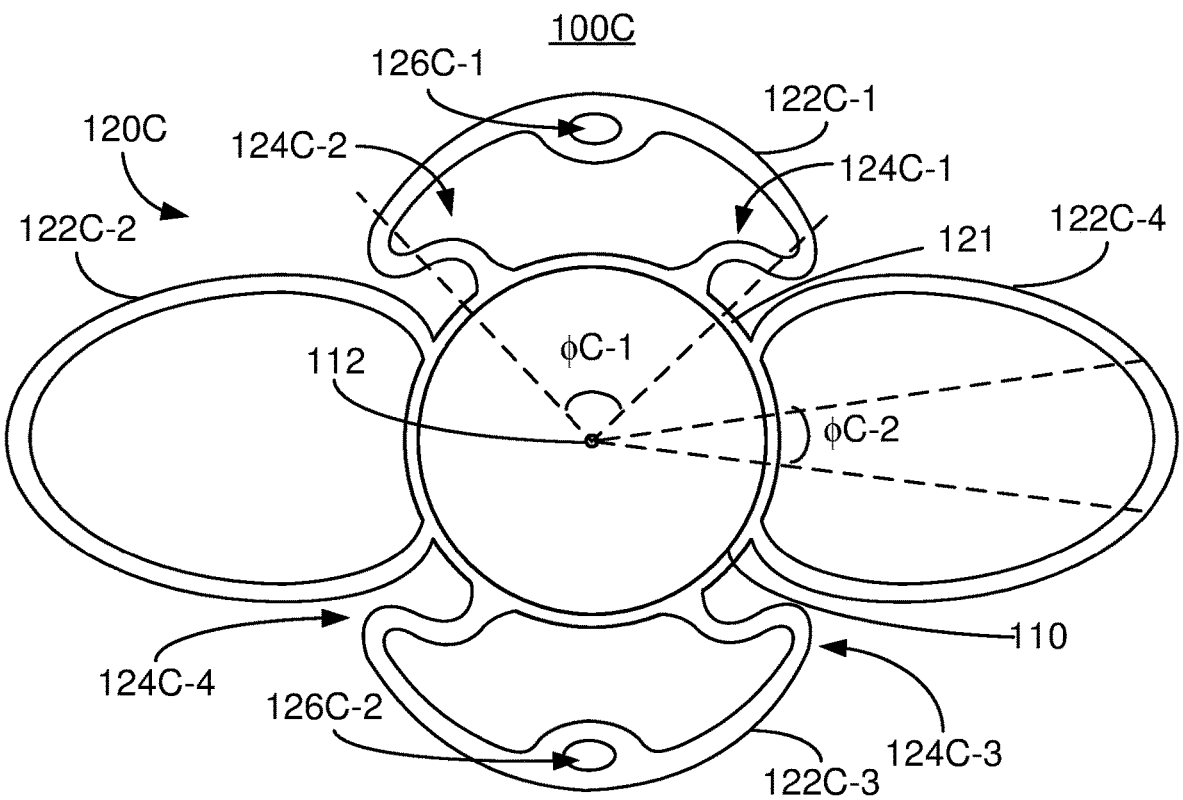
FIG. 3 depicts another exemplary embodiment of an ophthalmic device having a closed-loop haptic structure.

FIG. 3 depicts another exemplary embodiment of an ophthalmic device 100C having an optic 110 and a closed-loop haptic structure 120C. For simplicity, the ophthalmic device 100C is also referred to as an IOL 100C. The IOL 100C is similar to the IOL 100A and analogous components have similar labels. IOL 100C includes an optic 110 and closed-loop haptic structure 120C that are analogous to the optic 110 and closed-loop haptic structure 120A of FIGS. 1A-1D. Because optic 110 of IOL 100C is substantially the same as the optic 110 of IOL 100A, the optic 110 of IOL 100C will not be separately described with regard to FIG. 3. For clarity, FIG. 3 is not to scale and not all components may be shown.

Like the closed loop haptic structure 120A of IOL 100A, the closed-loop haptic structure 120C of IOL 100C may include a frame 121; closed loops 122C-1, 122C-2, 122C-3, and 122C-4 (collectively or generically 122C); hinges 124C-1/124C-2 (of closed loop 122C-1) and hinges124C-3/124C-4 (of closed loop 122C-3) (the hinges collectively or generically hinges 124C); centerline (not shown); and manipulation structures 126C-1 and 126C-2 (each of which are analogous to corresponding structures of IOL 100A). With regard to the hinges 124C, they may be configured and function in an analogous manner to the hinges 124A of IOL 100A. Similarly, manipulation structures 126C-1 and 126C-2 may be configured and function in an analogous manner to the manipulation structures 126A-1 and 126A-2 of IOL 100A.

The primary difference between IOL 100C and IOL 100A is the additional of additional closed-loops 122C-2 and 122C-4 to haptic structure 120C (as opposed the haptic structure 120A, which only includes closed-loop 122A-1 (corresponding to 122C-1) and closed loop 122A-2 (corresponding to 122C-3)). Closed-loops 122C-1 and 122C-3 may each span and ϕC-1, which may be analogous to angle ϕA described above with regard to IOL 100A. Moreover, closed-loops 122C-1 and 122C-3 may each be configured in a similar manner to closed-loops 122A-1 and 122A-2 described above with regard to IOL 100A.

In addition to closed-loops 122C-1 and 122C-3, IOL 100C may further include closed-loops122C-2 and 122C-4 each spanning an angle ϕC-2. In certain embodiments, angle ϕC-1 is larger than ϕC-2. Additionally, unlike closed-loops 122C-1 and 122C-3, closed-loops 122C-2 and 122C-4 may not include any hinges. Instead, the loops 122C-2 and 122C-4 merely bow outward from the attachment locations. In other embodiments, the loops 122C-2 and 122C-4 may be connected to the frame in a radial direction. In still other embodiments, one or more of the connections of the loops 122C-2 and/or 122C-4 to the frame 121 may take the form of a hinge. Thus, the loops 122C may be connected to the frame 121 using a mix of hinges 124C and radial or other connections.

For substantially the same reasons as discussed above with regard to IOL 100A, IOL 100C may improve patient outcomes by reducing incidence of PCO and improving refractive outcomes.

Figure 4:
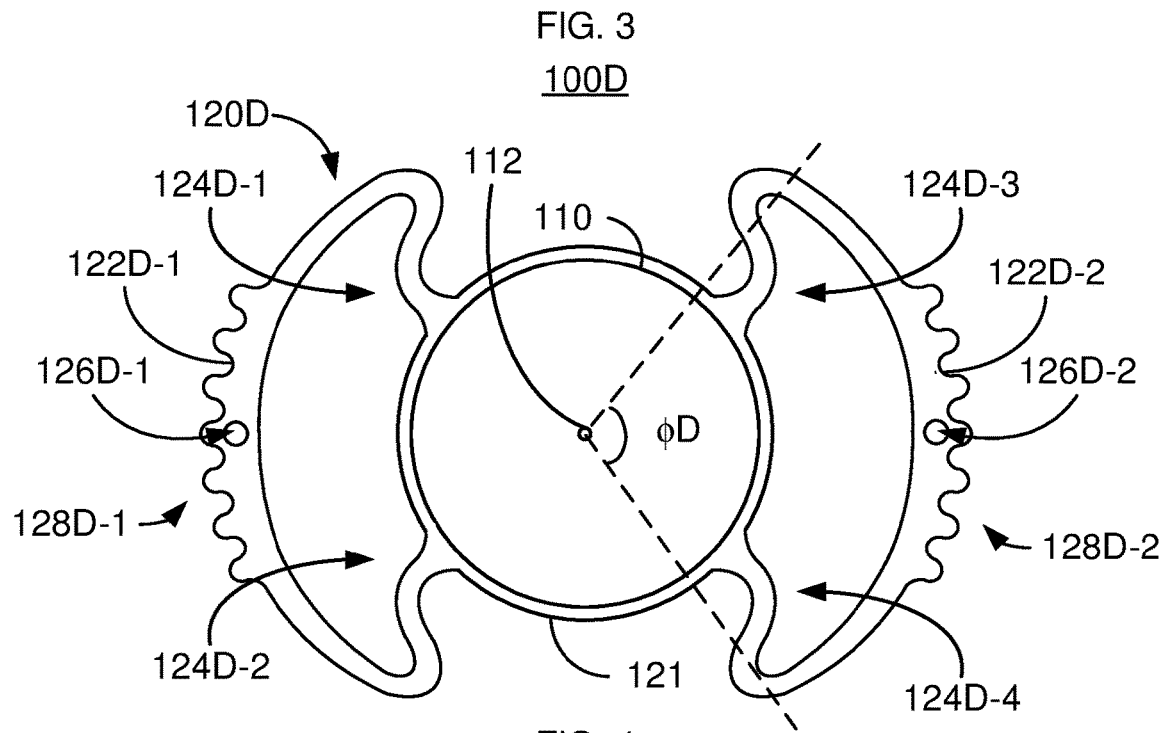
FIG. 4 depicts another exemplary embodiment of an ophthalmic device having a closed-loop haptic structure.

FIG. 4 depicts another exemplary embodiment of an ophthalmic device 100D having an optic 110 and a closed-loop haptic structure 120D. For simplicity, the ophthalmic device 100D is also referred to as an IOL 100D. The IOL 100D is similar to the IOL 100A and analogous components have similar labels. IOL 100D includes an optic 110 and closed-loop haptic structure 120D that are analogous to the optic 110 and closed-loop haptic structure 120A of FIGS. 1A-1D. Because optic 110 of IOL 100D is substantially the same as the optic 110 of IOL 100A, the optic 110 of IOL 100D will not be separately described with regard to FIG. 4. For clarity, FIG. 4 is not to scale and not all components may be shown.

Like the closed loop haptic structure 120A of IOL 100A, the closed-loop haptic structure 120D of IOL 100D may include a frame 121; closed loops 122D-1 and 122D-2 (collectively or generically 122D); hinges 124D-1, 124D-2 124D-3, and 124D-4 (collectively or generically hinges 124D); centerline (not shown); and manipulation structures 126D-1 and 126D-2 (each of which are analogous to corresponding structures of IOL 100A). With regard to the hinges 124D, they may be configured and function in an analogous manner to the hinges 124A of IOL 100A. Similarly, manipulation structures 126D-1 and 126D-2 may be configured and function in an analogous manner to the manipulation structures 126A-1 and 126A-2 of IOL 100A.

The primary difference between IOL 100D and IOL 100A is that, in IOL 100D, each of the loops 122D-1 and 122D-2 has a textured edge 128D-1 and 128D-2, respectively. The textured edges 128D-1 may take the form of a roughening of the surface of the edge, bumps/knobs, undulations or other texture(s) on the region of the loops 122D that may contact the capsular bag. The textured edges 128D-1 and 128D-2 may improve the ability of the loops 122D-1 and 122D-2 to remain stationary with respect to the sidewalls of the capsular bag. Thus, textures 122D-1 and 122D-2 may enhance the stability of the IOL 100D.

For substantially the same reasons as discussed above with regard to IOL 100A, IOL 100D may improve patient outcomes by reducing incidence of PCO and improving refractive outcomes. Additionally, the added features of IOL 100D (e.g., textured edges 128D-1 and 128D-2) may further enhance the stability benefits described above.

Figure 5:
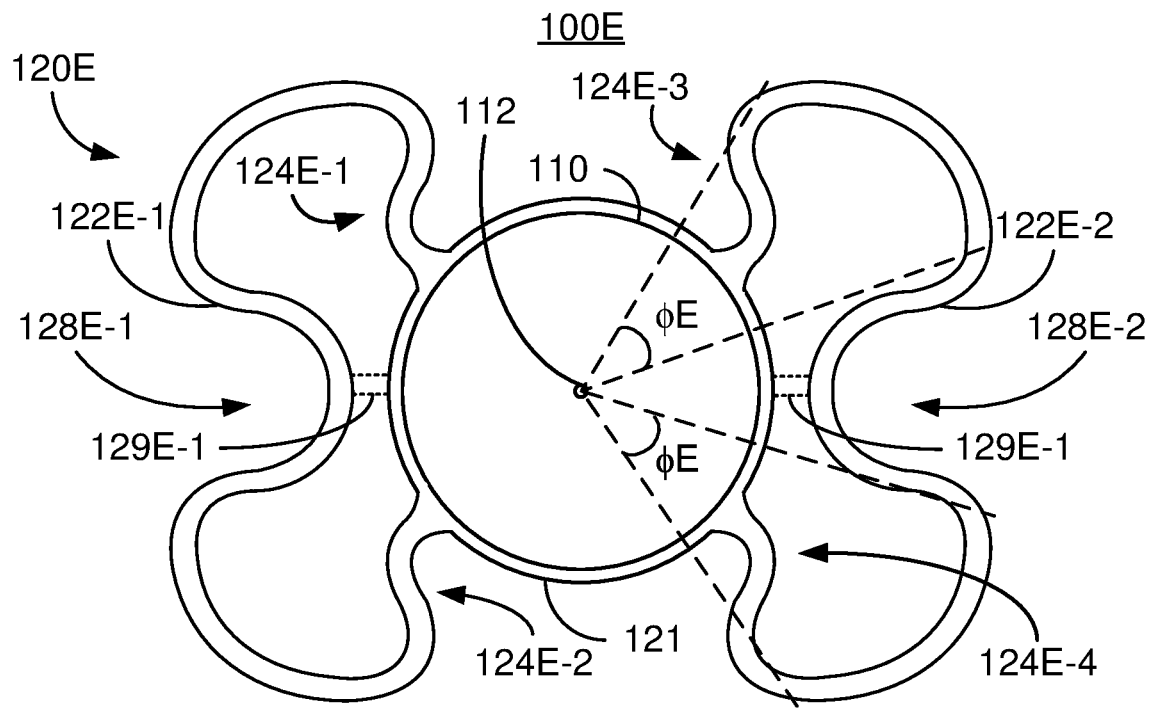
FIG. 5 depicts another exemplary embodiment of an ophthalmic device having a closed-loop haptic structure.

FIG. 5 depicts another exemplary embodiment of an ophthalmic device 100E having an optic 110 and a closed-loop haptic structure 120E. For simplicity, the ophthalmic device 100E is also referred to as an IOL 100E. The IOL 100E is similar to the IOL 100A and analogous components have similar labels. IOL 100E includes an optic 110 and closed-loop haptic structure 120E that are analogous to the optic 110 and closed-loop haptic structure 120A of FIGS. 1A-1D. Because optic 110 of IOL 100E is substantially the same as the optic 110 of IOL 100A, the optic 110 of IOL 100E will not be separately described with regard to FIG. 5. For clarity, FIG. 5 is not to scale and not all components may be shown.

Like the closed loop haptic structure 120A of IOL 100A, the closed-loop haptic structure 120E of IOL 100E may include a frame 121; closed loops 122E-1 and 122E-2 (collectively or generically 122E); hinges 124E-1, 124E-2 124E-3, and 124E-4 (collectively or generically hinges 124D); and centerline (not shown). Although no manipulation structures are shown in FIG. 5, the loop(s) 122E-1 and/or 122E-2 might each include one or more manipulation structures. With regard to the hinges 124E, they may be configured and function in an analogous manner to the hinges 124A of IOL 100A.

The primary difference between IOL 100D and IOL 100A is that, in IOL 100D, each of the loops 122E-1 and 122E-2 has a depression 128E-1 and 128E-2, respectively. The depressions 128E-1 and E-2 divide their respective closed-loops 122E into two portions each spanning an angle ϕE. This is because the outer portions of each loop 122E contact the capsular bag, while the depressions 128E-1 and 128E-2 do not.

For substantially the same reasons as discussed above with regard to IOL 100A, IOL 100E may improve patient outcomes by reducing incidence of PCO and improving refractive outcomes.

Figure 6:
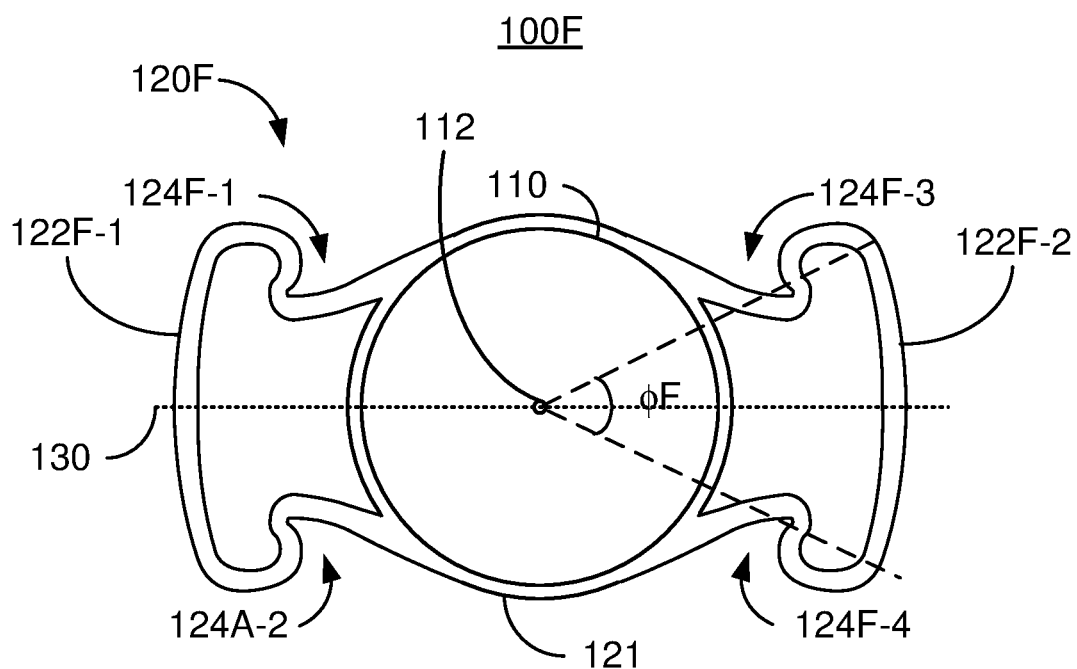
FIG. 6 depicts another exemplary embodiment of an ophthalmic device having a closed-loop haptic structure.

FIG. 6 depicts another exemplary embodiment of an ophthalmic device 100F having an optic 110 and a closed-loop haptic structure 120F. For simplicity, the ophthalmic device 100F is also referred to as an IOL 100F. The IOL 100F is similar to the IOL 100A and analogous components have similar labels. IOL 100F includes an optic 110 and closed-loop haptic structure 120F that are analogous to the optic 110 and closed-loop haptic structure 120A of FIGS. 1A-1D. Because optic 110 of IOL 100F is substantially the same as the optic 110 of IOL 100A, the optic 110 of IOL 100E will not be separately described with regard to FIG. 6. For clarity, FIG. 6 is not to scale and not all components may be shown.

Like the closed loop haptic structure 120A of IOL 100A, the closed-loop haptic structure 120F of IOL 100F may include a frame 121; closed loops 122F-1 and 122F-2 (collectively or generically 122F); hinges 124F-1, 124F-2, 124F-3 and 124F-4 (collectively or generically hinges 124F) and a centerline (not shown). Although no manipulation structures are shown in FIG. 6, the loops 122F-1 and/or 122F-2 might each include one or more manipulation structures.

The primary difference between IOL 100F and IOL 100A is that, in IOL 100F, hinges 124F are oriented differently than hinges 124A. This different configuration may cause hinges 124F to collapse inwardly in response to a compressive force (rather than outwardly, as described above with regard to IOL 100A).

For substantially the same reasons as discussed above with regard to IOL 100A, IOL 100E may improve patient outcomes by reducing incidence of PCO and improving refractive outcomes.

FIG. 7 depicts another exemplary embodiment of an ophthalmic device 100G having an optic 110 and a closed-loop haptic structure 120G. For simplicity, the ophthalmic device 100G is also referred to as an IOL 100G. The IOL 100G is similar to the IOL 100A and analogous components have similar labels. IOL 100G includes an optic 110 and closed-loop haptic structure 120G that are analogous to the optic 110 and closed-loop haptic structure 120A of FIGS. 1A-1D. Because optic 110 of IOL 100G is substantially the same as the optic 110 of IOL 100A, the optic 110 of IOL 100G will not be separately described with regard to FIG. 7. For clarity, FIG. 7 is not to scale and not all components may be shown.

Like the closed loop haptic structure 120E of IOL 100E, the closed-loop haptic structure 120G of IOL 100G may include a frame 121; closed loops 122F-1 and 122F-2 (collectively or generically 122F); hinges 124F-1, 124F-2, 124F-3 and 124F-4 (collectively or generically hinges 124F); a centerline (not shown); and depressions 128G-1 and 128G-2. Although no manipulation structures are shown in FIG. 7, the loops 122G-1 and/or 122G-2 might each include one or more manipulation structures.

The primary difference between IOL 100G and IOL 100E is that, in IOL 100G, closed-loops 122G includes wingtips 132-1 and 132-2 and wingtips 132-3 and 132-4 (collectively and generically 132). In the embodiment shown, the wingtips 132 extend from the loops 122G in substantially the same direction as the curvature of the loops 122G. Stated differently, the wingtips 132 follow the curvature of the loops 122G. In other embodiments, the wingtips 132 may be oriented in another manner. However, the wingtips 132 are generally desired be at a nonzero angle from the radial direction and more closely aligned with the CCW or CW direction. The wingtips 132 may increase the angles ϕG spanned by the two portions of each of the loops 122G because the wingtips 132.

For substantially the same reasons as discussed above with regard to IOL 100A, IOL 100G may improve patient outcomes by reducing incidence of PCO and improving refractive outcomes. Additionally, the added features of IOL 100D (e.g., wingtips 132 that extend the angle of contact of closed loops 122G) may further enhance the stability benefits described above.

FIGS. 8A-8C depict various view of another exemplary embodiment of an ophthalmic device 100H having an optic 110 and a closed-loop haptic structure 120H. For simplicity, the ophthalmic device 100H is also referred to as an IOL 100H. FIG. 8A depicts a perspective view of the IOL 100H. FIG. 8B depicts a plan view of the IOL 100H. FIG. 8C depicts a side view of the IOL 100H. IOL 100H includes an optic 110 and closed-loop haptic structure 120H that are analogous to the optic 110 and closed-loop haptic structure 120A of FIGS. 1A-1D. Because optic 110 of IOL 100G is substantially the same as the optic 110 of IOL 100A, the optic 110 of IOL 100G will not be separately described with regard to FIG. 7. For clarity, FIG. 7 is not to scale and not all components may be shown.

Like the closed loop haptic structure 120A of IOL 100A, the closed-loop haptic structure 120H of IOL 100H may include a frame 121; closed loops 122H-1 and 122H-2 (collectively or generically 122H) and a centerline (not shown). Although no manipulation structures and hinges are shown in FIG. 8, the loops 122H-1 and/or 122H-2 might each include one or more manipulation structures and/or hinges. For example, the connections 124H-1, 124H-2, 124H-3 and 124H-4 are shown as being substantially radial. In other embodiments, one or more of the connections 124H-1, 124H-2, 124H-3 and 124H-4 may take the form of hinges. The closed-loop haptic structure 120H also includes vaulting structures 134-1 and 134-2 (collectively or generically 134).

The closed loops 122H and the vaulting structures 134 may hold the IOL 100H in position in the patient's eye by contacting the capsular bag. Each of the loops 122H spans an angle, ϕH. Thus, the loops 122H may stretch the capsular bag to a greater extent than an open arm haptic, improving stability and reducing striae. The vaulting structures 134 are in a different plane from the loops 122H. The vaulting structures 134 extend from the loops 122H in a direction substantially parallel to the optic axis 112. In the embodiment shown, the loops 122H are also shown as being in a different plane than the optic 110 and frame 121. The vaulting structures 134 thus extend the capsular bag in a direction out of plane from the optic 110. Thus, the capsular bag may be further stretched. The vaulting structures 134 may thus reduce striae and improve stability of the IOL 100H.

For substantially the same reasons as discussed above with regard to IOL 100A, IOL 100H may improve patient outcomes by reducing incidence of PCO and improving refractive outcomes. Additionally, the presence of the vaulting structures 134 may further improve the stability and reduce the striae for of IOL 100H.

It will be appreciated that various of the above-disclosed and other features and functions, or alternatives thereof, may be desirably combined into many other different devices or applications. It will also be appreciated that various presently unforeseen or unanticipated alternatives, modifications, variations or improvements therein may be subsequently made by those skilled in the art which alternatives, variations and improvements are also intended to be encompassed by the following claims.

The invention claimed is:

1. An intraocular lens (IOL), comprising:
an optic including an optic axis;
a closed-loop haptic coupled to the optic and extending substantially along a first plane perpendicular to the optic axis, the closed-loop haptic comprising:
a first hinge at a first attachment point to the optic, the first hinge comprising a meandering configuration; and
a second hinge at a second attachment point to the optic;
wherein the first hinge and the second hinge are sized and configured to compress such that the closed-loop haptic is substantially compressed inwardly towards the optic axis while remaining substantially in the first plane perpendicular to the optic axis during compression; and
a frame surrounding the optic, and wherein the closed-loop haptic is coupled to the optic at the first attachment point and the second attachment point via the frame,
wherein the optic is positioned in a second plane substantially perpendicular to the optic axis, and wherein the second plane is located posterior to the first plane,
wherein the intraocular lens is configured such that the entire optic substantially remains extending along the second plane during compression of the first hinge and the second hinge,
wherein the first attachment point extends radially and orthogonally from the frame.

2. The intraocular lens of claim 1, wherein an outer edge of the closed-loop haptic comprises a textured surface.

3. The intraocular lens of claim 1, wherein the closed-loop haptic includes a manipulation structure formed therein.

4. The intraocular lens of claim 1, wherein the closed-loop haptic includes a depression opposite to the optic.

5. The intraocular lens of claim 1, wherein the frame comprises a cross-sectional thickness greater than that of an edge of the optic.

6. The intraocular lens of claim 1,
wherein the meandering configuration of the first hinge includes a first section, a second section, and a first connecting section between the first section and the second section, the first section having a first component extending in a first angular direction, the second section having a second component extending in a second angular direction, wherein the second angular direction is opposite to the first angular direction;
wherein the second hinge comprises a meandering configuration including a third section, a fourth section, and a second connecting section between the third section and the fourth section, the third section having a third component extending in the second angular direction, and the fourth section having a fourth component extending in the first angular direction; and the second section is connected to the fourth section to form the closed-loop haptic.

7. The intraocular lens of claim 6, wherein the first direction is clockwise, and the second direction is counter-clockwise.

8. The intraocular lens of claim 1, further comprising a second closed-loop haptic coupled to the optic.

9. The intraocular lens of claim 8, wherein the second closed-loop haptic is configured to contact a capsular bag along a smaller angular distance than the closed-loop haptic.

10. The intraocular lens of claim 8, further comprising a third closed-loop haptic coupled to the optic.

11. The intraocular lens of claim 1, wherein the closed-loop haptic has an angular span of at least 90 degrees.

12. The intraocular lens of claim 11, wherein the angular span corresponds to the angle spanned by the closed-loop haptic over which the closed-loop haptic is configured to contact a capsular bag.

13. The intraocular lens of claim 11, wherein the closed-loop haptic has an angular span of at least 120 degrees.

14. The intraocular lens of claim 11, further comprising a second closed-loop haptic coupled to the optic and extending substantially along the first plane perpendicular to the optic axis, wherein the second closed-loop haptic has an angular span of at least 90 degrees.

15. The intraocular lens of claim 14, further comprising a third closed-loop haptic coupled to the optic and extending substantially along the plane perpendicular to the optic axis, wherein the third closed-loop haptic has an angular span of at least 90 degrees.

* * * * *